(12) United States Patent
Allen

(10) Patent No.: US 8,739,363 B2
(45) Date of Patent: Jun. 3, 2014

(54) REMOVABLE GROMMET DEVICE WITH ENLARGEABLE SLIT AND METHOD THEREOF

(75) Inventor: Kraig Herman Allen, Leesburg, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 0 days.

(21) Appl. No.: 13/614,207

(22) Filed: Sep. 13, 2012

(65) Prior Publication Data

US 2013/0064734 A1    Mar. 14, 2013

Related U.S. Application Data

(60) Provisional application No. 61/534,650, filed on Sep. 14, 2011.

(51) Int. Cl.
*F16L 5/00*    (2006.01)

(52) U.S. Cl.
USPC .................................................. 16/2.1; 16/2.2

(58) Field of Classification Search
USPC .................. 16/2.1–2.3; 174/153 G, 655, 660; 248/56, 60
See application file for complete search history.

(56) References Cited

U.S. PATENT DOCUMENTS

| | | |
|---|---|---|
| 2,438,499 A | 3/1948 | Hartman |
| 2,664,458 A | 12/1953 | Rapata |
| 3,110,337 A | 11/1963 | Biesecker |
| 3,217,584 A | 11/1965 | Amesbury |
| 3,245,428 A * | 4/1966 | Klimak et al. ............... 137/493 |
| 3,309,955 A | 3/1967 | Turnbull et al. |
| 3,516,111 A * | 6/1970 | Kerry ............................. 16/2.1 |
| 3,611,861 A | 10/1971 | Schulze |
| 3,651,734 A | 3/1972 | McSherry |
| 3,678,797 A | 7/1972 | Seckerson |
| 3,964,364 A | 6/1976 | Pie |
| 4,136,599 A | 1/1979 | Hammer, Jr. |
| 4,276,806 A | 7/1981 | Morel |
| 4,843,675 A | 7/1989 | Diamantis |
| 5,518,115 A | 5/1996 | Latulippe |
| 5,525,314 A | 6/1996 | Hurson |
| 5,645,282 A | 7/1997 | Belter |
| 5,702,076 A * | 12/1997 | Humber ......................... 248/57 |
| 5,775,859 A | 7/1998 | Anscher |
| 5,954,345 A * | 9/1999 | Svoboda et al. ............. 277/626 |
| 5,975,820 A | 11/1999 | Kirchen |
| 6,099,812 A | 8/2000 | Allen et al. |
| 6,364,586 B1 | 4/2002 | Okada |
| 6,382,575 B1 | 5/2002 | Frush et al. |
| 6,505,386 B1 | 1/2003 | Allie |
| 6,514,023 B2 | 2/2003 | Moerke |

(Continued)

*Primary Examiner* — Roberta Delisle
(74) *Attorney, Agent, or Firm* — Hayes Soloway P.C.

(57) ABSTRACT

A grommet device and method of using a grommet device is provided. The grommet device includes a substantially circular base structure. A substantially circular top structure is connected to the substantially circular base structure with a substantially cylindrical middle portion, wherein an aperture having an interior space is positioned interior of the substantially cylindrical middle portion. A flexible top surface is connected to the substantially circular top structure, wherein the flexible top surface is substantially planar. At least one enlargeable slit is formed within the flexible top surface and through an entire thickness of the flexible top surface, wherein an unobstructed path is positioned from a location proximate to an exterior side of the flexible top surface, through the at least one enlargeable slit, and into the interior space of the aperture.

13 Claims, 6 Drawing Sheets

(56) References Cited

U.S. PATENT DOCUMENTS

| | | | |
|---|---|---|---|
| 6,694,566 B1 * | 2/2004 | Mockett | 16/2.1 |
| 6,710,249 B1 * | 3/2004 | Denton | 174/651 |
| 6,854,946 B2 | 2/2005 | Bauer | |
| 6,895,634 B2 * | 5/2005 | Tisbo | 16/2.1 |
| 7,579,556 B2 * | 8/2009 | Tapper | 174/650 |
| 7,579,557 B2 * | 8/2009 | Tapper | 174/650 |
| 7,582,836 B2 * | 9/2009 | Tapper | 174/650 |
| 7,615,714 B2 * | 11/2009 | Pyron et al. | 174/660 |
| 2006/0261695 A1 | 11/2006 | Terrill et al. | |
| 2007/0138042 A1 | 6/2007 | Wood | |
| 2007/0205123 A1 | 9/2007 | Bettenhausen et al. | |
| 2010/0065456 A1 | 3/2010 | Junk et al. | |
| 2011/0014005 A1 | 1/2011 | Shinozaki | |
| 2011/0091301 A1 | 4/2011 | Shimizu et al. | |
| 2011/0170982 A1 | 7/2011 | Watanabe | |
| 2011/0197405 A1 | 8/2011 | Kato et al. | |

* cited by examiner

REMOVABLE GROMMET DEVICE WITH ENLARGEABLE SLIT AND METHOD THEREOF

CROSS REFERENCE TO RELATED APPLICATION

This application claims benefit of U.S. Provisional Application Ser. No. 61/534,650, entitled, "Removable Grommet Device and Method Thereof" filed Sep. 14, 2011, the entire disclosure of which is incorporated herein by reference.

FIELD OF THE DISCLOSURE

The present disclosure is generally related to grommets and more particularly is related to a removable grommet device with enlargeable slit and method thereof.

BACKGROUND OF THE DISCLOSURE

Within the medical industry, there is a need for holding a variety of medical instruments for various purposes. For example, a surgeon needs to be able to access medical instruments for surgery quickly, a dentist needs to be able to access his or her dental tools, and virtually all medical instruments must be placed within a holder during a sterilization process. Conventional holding containers may include a variety of bases holding insertable trays that have specifically-designed areas for holding specific tools. However, with smaller tools, such as small dental tools, it is frequently inefficient to store them in these containers, since they're prone to being moved around and jostled as the container is moved. This may result in a grouping of smaller tools in one area, which means that the surgeon or medical staff member must sift through the grouping to locate a specific tool.

Conventionally, medical instruments are often held in containers or trays with holes and grommets. The grommets may be positioned within the hole and provide a secure interface between the medical instrument and the hole within the container or tray. Often, the grommets are sized to match a certain shaft size of a medical instrument, and a container or tray may include a variety of different sized grommets, each specifically engineered and designed to hold one of a variety of medical instruments. These medical instruments have varying shaft sizes and it often becomes tedious to search for the appropriately sized grommet that matches a particular shaft size of the medical instrument. It is not uncommon for a medical tray to have fifty or more grommets, with a dozen or more different sizes. Thus, the time it takes to match a specific medical instrument to a specifically sized grommet may result in inefficient use of valuable time.

Most grommets in use today are intended to be permanent fixtures in medical sterilization trays, in that they are not designed to be removed on a regular basis. This is due to the high risk of harboring bacteria and other contaminants within the spaces, crevices and other areas exposed when the grommet is removed from the tray. When the grommets are permanently installed within the holes, with the surfaces of the grommets forming tight seals with the container or the tray. This may prevent bacteria from becoming lodged within cracks, crevices or other areas, which may prevent complete sterilization of the medical tool. However, users often try and remove the grommets when they become damaged, or when they desire to reposition the grommet in a new location. This removal of the grommet may result in damage to the grommet structure itself, as well as present additional areas for harboring bacteria.

Thus, a heretofore unaddressed need exists in the industry to address the aforementioned deficiencies and inadequacies.

SUMMARY OF THE DISCLOSURE

Embodiments of the present disclosure provide a grommet device. Briefly described, in architecture, one embodiment of the system, among others, can be implemented as follows. The grommet device has a substantially circular base structure. A substantially circular top structure is connected to the substantially circular base structure with a substantially cylindrical middle portion, wherein an aperture having an interior space is positioned interior of the substantially cylindrical middle portion. A flexible top surface is connected to the substantially circular top structure, wherein the flexible top surface is substantially planar. At least one enlargeable slit is formed within the flexible top surface and through an entire thickness of the flexible top surface, wherein an unobstructed path is positioned from a location proximate to an exterior side of the flexible top surface, through the at least one enlargeable slit, and into the interior space of the aperture.

The present disclosure can also be viewed as providing a system for sterilizing a medical instrument. Briefly described, in architecture, one embodiment of the system, among others, can be implemented as follows. A medical instrument sterilization platform has a plurality of holes formed therein. A grommet device is positioned in one of the plurality of holes of the medical instrument sterilization platform, wherein the grommet device has a substantially circular base structure connected to a substantially circular top structure with a substantially cylindrical middle portion, wherein the substantially circular top structure is positioned on a first side of the medical instrument sterilization platform and the substantially circular base structure is positioned on a second side of the medical instrument sterilization platform, wherein the first side is positioned opposite the second side. An aperture defined by the substantially cylindrical middle portion is positioned substantially concentrically of the one of the plurality of holes. A flexible top surface is integrally connected to the substantially circular top structure, wherein the flexible top surface has at least one enlargeable slit formed therein, wherein the medical instrument is frictionally retained in a substantially stationary position by the flexible top surface within the at least one enlargeable slit and at least partially within the aperture.

The present disclosure can also be viewed as providing a method of securing a medical instrument with a medical sterilization platform. In this regard, one embodiment of such a method, among others, can be broadly summarized by the following steps: positioning a grommet device within a hole of a medical sterilization platform, wherein an aperture of the grommet device is positioned substantially concentric with the hole; inserting the medical instrument through at least one enlargeable slit formed within a flexible top surface of the grommet device, thereby positioning at portion of the medical instrument within the aperture of the grommet device; and frictionally retaining the medical instrument in a substantially stationary position within the aperture of the grommet device with the flexible top surface of the grommet device while subjecting the medical instrument to a sterilization process.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
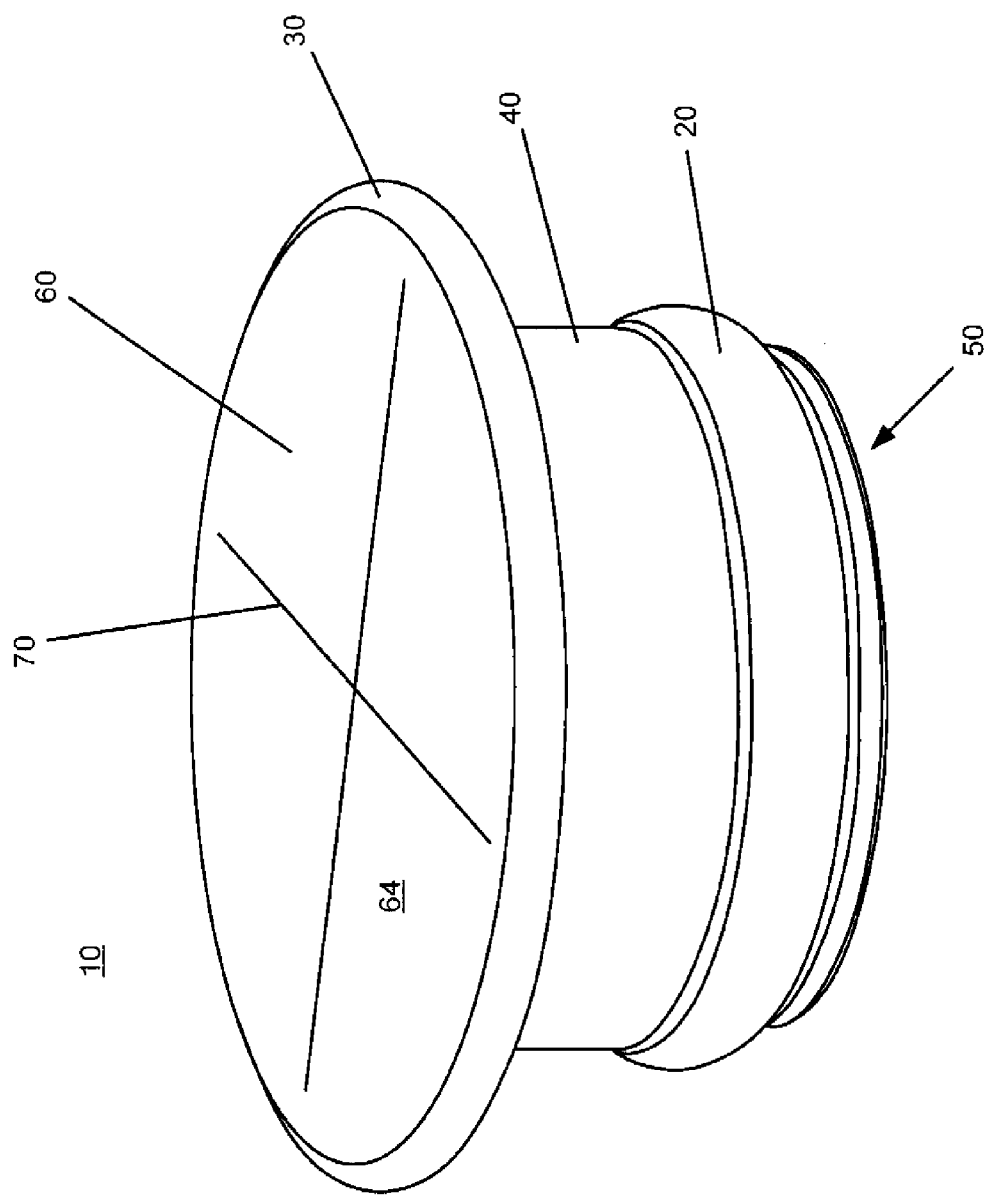
FIG. 1 is a plan view illustration of a grommet device, in accordance with a first exemplary embodiment of the present disclosure.

FIG. 1 is a plan view illustration of a grommet device 10, in accordance with a first exemplary embodiment of the present disclosure. The grommet device 10, which may be referred to as 'device 10,' includes a substantially circular base structure 20 and a substantially circular top structure 30 connected to the substantially circular base structure 20 with a substantially cylindrical middle portion 40. An aperture 50 having an interior space 52 (FIG. 2) is positioned interior of the substantially cylindrical middle portion 40. A flexible top surface 60 is connected to the substantially circular top structure 30, wherein the flexible top surface 60 is substantially planar. At least one enlargeable slit 70 is formed within the flexible top surface 60 and through an entire thickness 62 (FIG. 2) of the flexible top surface 60, wherein an unobstructed path 76 (FIG. 2) is positioned from a location proximate to an exterior side 64 of the flexible top surface 60, through the at least one enlargeable slit 70, and into the interior space 52 (FIG. 2) of the aperture 50.

The device 10 may be used with medical sterilization platforms and medical instrument or tool holding structures, such as sterilization trays, which are used to hold medical instruments during a sterilization process. The device 10 fits within a hole within the medical sterilization platform to provide an interface between the medical sterilization platform and the medical instrument that it is holding. Accordingly, the device 10 may be used in any industry utilizing medical tools, such as tools, instruments, or any other type of implement used for surgical procedures, operations, or other medical procedures. These medical instruments may often have a shaft portion or elongated section that is sized to fit within the device 10. The device 10 may be used to hold medical instruments in surgical environments before, during and/or after a surgical procedure, or a medical instrument sterilization process. Similarly, the device 10 may be used with dental instruments for dental operations, routine cleanings, or for any other use. Other settings and uses within the medical field are also envisioned, all of which are considered within the scope of the present disclosure.

Figure 2:
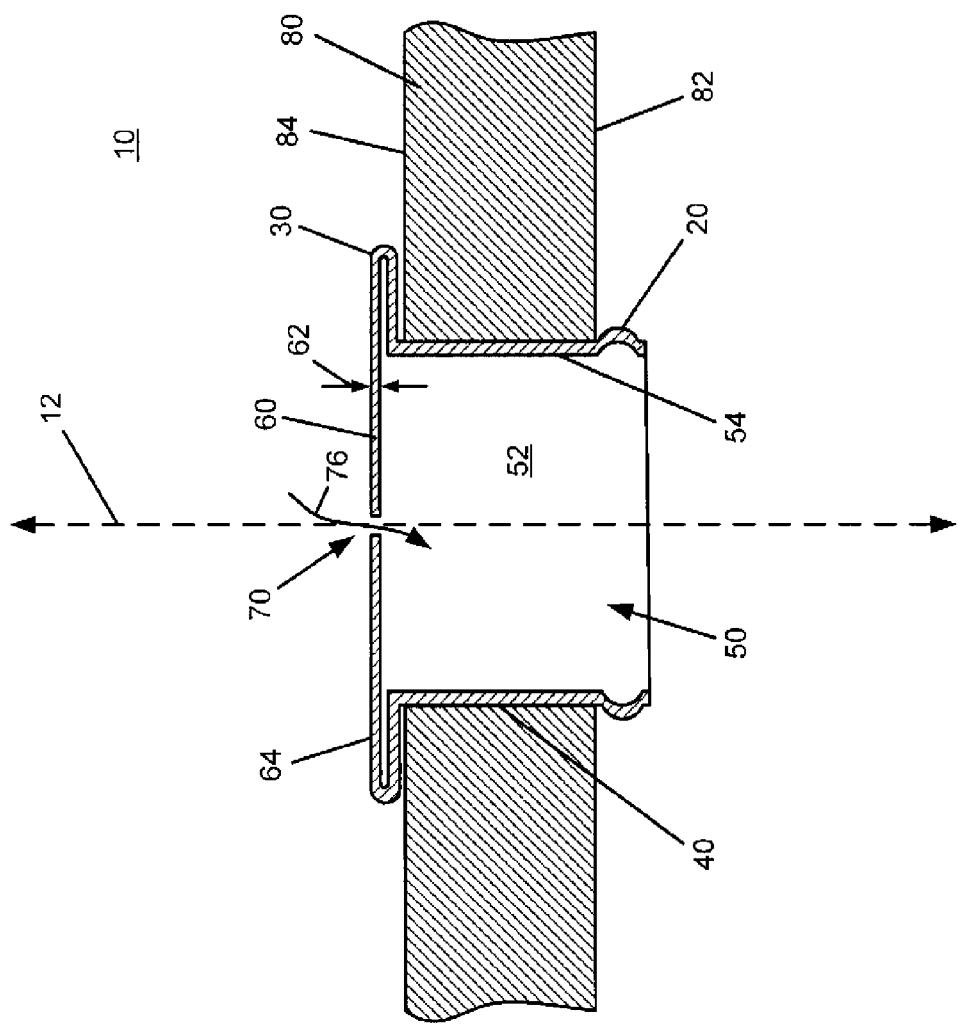
FIG. 2 is a cross-sectional view illustration of the grommet device, in accordance with the first exemplary embodiment of the present disclosure.

FIG. 2 is a cross-sectional view illustration of the grommet device 10, in accordance with the first exemplary embodiment of the present disclosure. Specifically, the grommet device 10 is illustrated positioned within a hole of a medical sterilization platform 80. Commonly, the hole within the medical sterilization platform 80 will be a substantially cylindrical hole that is suited to receive a device 10 that has a substantially cylindrical profile. As such, the substantially circular base structure 20, the substantially circular top structure 30, and the substantially cylindrical middle portion 40 may each be sized to engage with the hole of the medical sterilization platform 80 with the desired tolerances. Of course, the hole within the medical sterilization platform 80 may not be perfectly circular or cylindrical, in which case a device 10 have a matching profile may be used. In other words, the device 10 may commonly have circular components to match a circular-shaped hole within the medical sterilization platform 80, however the device 10 may be sized to match a hole having any shape. For clarity in disclosure, the substantially circular base structure 20, the substantially circular top structure 30, and the substantially cylindrical middle portion 40 may be described herein simply as the base structure 20, the top structure 30, and the middle portion 40.

The device 10 may be formed with the various components integrally or non-integrally affixed together. Commonly, the device 10 will be formed with integral components such that device is a substantially unitary structure. Alternatively, various parts or components of the device 10 may be formed separately and permanently or non-permanently affixed together. Commonly, the device 10 may be constructed from a rubber or silicon material that is substantially resistant to degradation from use and from sterilization environments. Within the medical industry, medical instruments are often sterilized in autoclaves, which utilize high temperatures, high pressures, moisture, and/or chemicals to sterilize a medical instrument.

As is shown in FIGS. 1-2, the base structure 20 of the device may be configured to be placed on a first side 82 of a medical sterilization platform 80 and the top structure 30 may be positioned on a second side 84 of the medical sterilization platform 80, where the first and second sides 82, 84 oppose each other. The medical sterilization platform 80 which may be an opening, hole, or aperture within a medical sterilization tray or other, similar structure. The base structure 20 may be sized slightly larger than the medical sterilization platform 80, thereby allowing the base structure 20 to be biased into position. For example, many sterilization trays include a plurality of holes for holding medical instruments. To secure the medical instrument properly during a medical sterilization process, the device 10 may be inserted into the hole by pushing the base structure 20 through the hole until the base structure 20 is located on one side of the tray, and the top structure 30 is located on an opposing side of the tray. Accordingly, the hole may be the medical sterilization platform 80. In this position, the base structure 20 may be positioned interior of, or below the medical sterilization platform 80.

Similar to the base structure 20, the top structure 30 may be sized larger than the medical sterilization platform 80. The large size of the top structure 30 may prevent the device 10 from slipping or moving out of position within the medical sterilization platform 80. However, in comparison with the base structure 20, the top structure 30 may be sized larger to allow the device 10 to be inserted into the medical sterilization platform 80 by pushing the base structure 20 through the medical sterilization platform 80 until the middle portion 40 is properly located within the medical sterilization platform 80. In this position, the larger top structure 30, in comparison to the base structure 20, may prevent the device 10 from moving further into the medical sterilization platform 80. Accordingly, the larger top structure 30 may be designed such that it is unable to be pushed into, or through, the medical sterilization platform 80.

It is noted that the base structure 20 and the top structure 30 may be sized to allow for easy insertion and removal of the device 10. This may be needed when the device 10 is intended to be disposable on a regular basis, such as after one use or just a few uses. Conventional grommets are not generally intended to be removable or disposable, and therefore may not be sized for convenient removal from the medical sterilization platform 80. When conventional grommets are removed, it is often a long and labor-intensive process, since their structures are not accommodating for removal. The device 10, on the other hand, may be removed to expose the spaces between the device 10 and the medical sterilization platform 80, thereby allowing these spaces to be cleaned and sterilized. This ability may prevent the harboring of bacteria in spaces where sterilant often cannot reach. Accordingly, the device 10 may be considered disposable, in that a new device 10 may be used each time a device 10 is needed, which may assure a higher degree of cleanliness, thereby providing a safer environment for medical instruments.

The middle portion 40 may integrally connect the base structure 20 to the top structure 30 such that the base and top structures 20, 30 are positioned below and above the medical sterilization platform 80, and the middle portion is positioned in an abutting location with an inner wall of the hole of the medical sterilization platform 80. The aperture 50 may be positioned within the device 10, interior of the middle portion 40 and generally between the base structure 20 and the top structure 30. In other words, the aperture 50 is a cavity, a cut-out of material, or hole, which is positioned within the device 10, commonly aligned along a central axis 12 of the cylindrical shape of the device 10. This central axis 12 may run through a center point of the medical sterilization platform 80, or may be positioned off-center, as various designs may dictate. The aperture 50 may be sized to hold any type of medical instrument, and thus, may have any size diameter. The aperture 50 includes an interior space 52, which may be defined by the aperture sidewall 54, i.e., the inner wall surface of the middle portion 40. The interior space 52 may be characterized as the space within the aperture 50 that is surrounded by the aperture sidewall 54.

Any of the components of the device 10, including the base and top structures 20, 30, the middle portion 40 and the aperture 50, may have any sizes. For example, a variety of interior and exterior diameters, thicknesses, or other dimensions may be included with the device 10. It may be common for a radial dimension of the base structure 20 to be larger than a radial dimension of the middle portion 40. Likewise, a radial dimension of the top structure 30 may be larger than a radial dimension of the middle portion 40. These dimensions may allow for proper positioning of the device 10 within the medical instrument platform 80. The overall dimensions of the device 10, including the overall thickness and external diameter may have any size. For example, the device 10 may be constructed with different overall sizes to accommodate various types of medical instruments, or various medical instrument platforms 80. All variations are considered within the scope of the present disclosure.

The flexible top surface 60 is connected to the top structure 30, as is shown in FIGS. 1-2. The flexible top surface 60 may be constructed from a flexible material, such as silicon, thereby allowing the flexible top surface 60 to flex and move when contacted by a medical instrument. The overall shape and size of the flexible top surface 60 may vary according to the design and intended use of the device 10. For example, as is shown in FIGS. 1-2, the flexible top surface 60 may be a substantially planar structure that is connected on all sides to the top structure 30. The flexible top surface 60 has one or more enlargeable slits 70, which are positioned within the flexible top surface 60 and directly abuts the aperture 50. The enlargeable slit 70 is formed through an entire thickness 62 of the flexible top surface 60 such that an unobstructed path 76 (identified with an arrow) is positioned from the exterior side 64 of the flexible top surface 60, through the flexible top surface 60, and into the aperture 50.

The enlargeable slit 70 formed within the flexible top surface 60 may substantially intersects a central axis 12 of the aperture 50. In other words, the enlargeable slit 70 may pass through the center point of the flexible top surface 60, among other locations of the flexible top surface 60 that the enlargeable slit 70 may pass through. Although this disclosure is described as having one enlargeable slit 70, the device 10 may include any number of enlargeable slits 70 within the flexible top surface 60. For example, two enlargeable slits 70 may be formed within the flexible top surface 60 and through an entire thickness 62 of the flexible top surface 60. In most circumstances when more than one enlargeable slit 70 is used, the enlargeable slits 70 may intersect each other. For example, it may be common for two enlargeable slits 70 to intersect each other in a substantially perpendicular orientation, depicted best in FIG. 3.

The enlargeable slit 70 may be formed in a variety of ways. For example, the enlargeable slit 70 may be formed from a plurality of slots within the flexible top surface 60, which allow the flexible top surface 60 to be biased away from an original or natural position, i.e., the substantially planar position. The individual portions of the flexible top surface 60 may be characterized as biasable sections of the flexible top surface 60, wherein the enlargeable slits 70 may define the various biasable sections within flexible top surface 60. Each of the biasable sections of the flexible top surface 60 may be biased or moved to enlarge the natural size of the enlargeable slit 70 to create an opening in the flexible top surface 60 large enough to fit a medical instrument. The size of the enlargeable slit 70 may vary greatly. For example, as is best shown in FIG. 1, a length dimension of the enlargeable slit 70 may be greater than a diameter dimension of the middle portion 40; however the enlargeable slit 70 may have any length or width measurement. It is noted that the enlargeable slit 70 may include a variety of different configurations, such as an enlargeable slit 70 that is substantially circular or oval shaped, wherein the perimeter materials forming the circular or oval shape may be stretched to enlarge the enlargeable slit 70. Yet another way of forming the enlargeable slit 70 may include manufacturing a plurality of parallel slots within the flexible top surface 60, wherein a medical instrument can be inserted within one of the slots.

Figure 3:
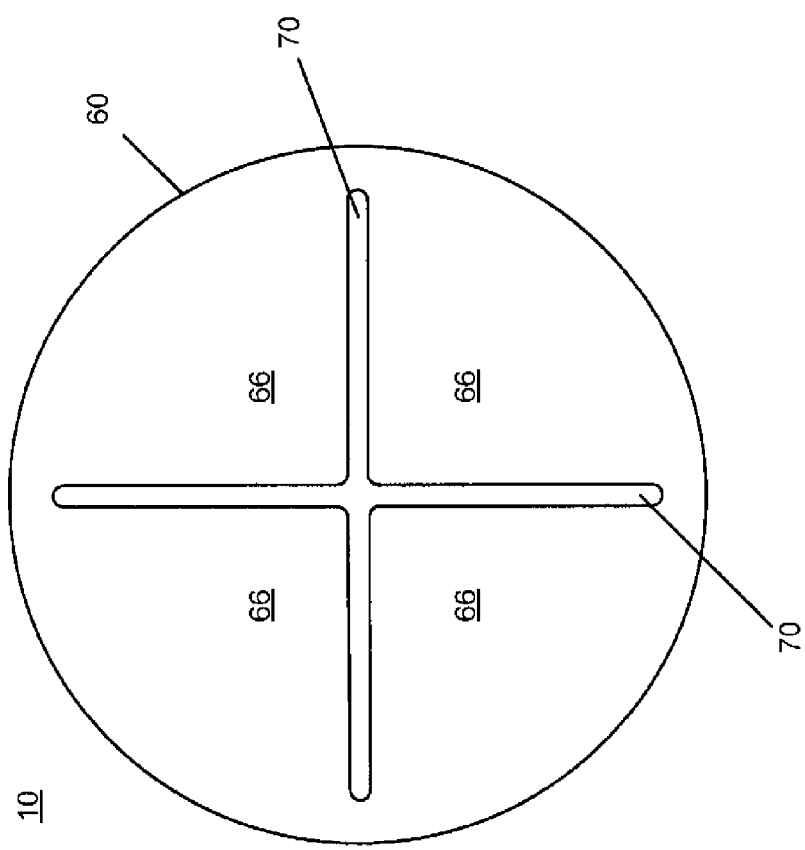
FIG. 3 is a top view illustration of the grommet device, in accordance with the first exemplary embodiment of the present disclosure.

FIG. 3 is a top view illustration of the grommet device 10, in accordance with the first exemplary embodiment of the present disclosure. The flexible top surface 60 may have an enlargeable slit 70 with any shape, such as bisecting slots as is shown in FIG. 3, or other shapes such as circles, ovals, parallel slots, etc. The overall dimensions of the enlargeable slit 70 may vary, depending on the design of the device 10, all of which are considered within the scope of the present disclosure. Of course, since the enlargeable slit 70 is designed to be enlargeable, the size of the enlargeable slit 70 may vary when the device 10 is being used or not being used.

As is shown in FIG. 3, the two enlargeable slits 70 formed within the flexible top surface 60 may define four biasable sections 66 of the flexible top surface 60. Each of the biasable sections 66 in FIG. 3 includes a portion of the flexible top surface 60 that is proximate to one or more of the enlargeable slits 70. When there is no medical instrument positioned within the device 10, as is depicted in FIG. 3, the biasable sections 66 may be in a non-biased position, such that the enlargeable slits 70 are positioned between of the biasable sections 66, respectively. When in the non-biased position, the biasable sections 66 may be substantially coplanar. On the other hand, when the medical instrument is positioned within the device 10 (FIG. 4), the biasable sections 66 may be in a biased position, where the enlargeable slits 70 are enlarged enough to create an opening to the interior space 52 of the aperture 50. The opening size will vary depending on the size of the medical instrument inserted within the device 10.

Figure 4:
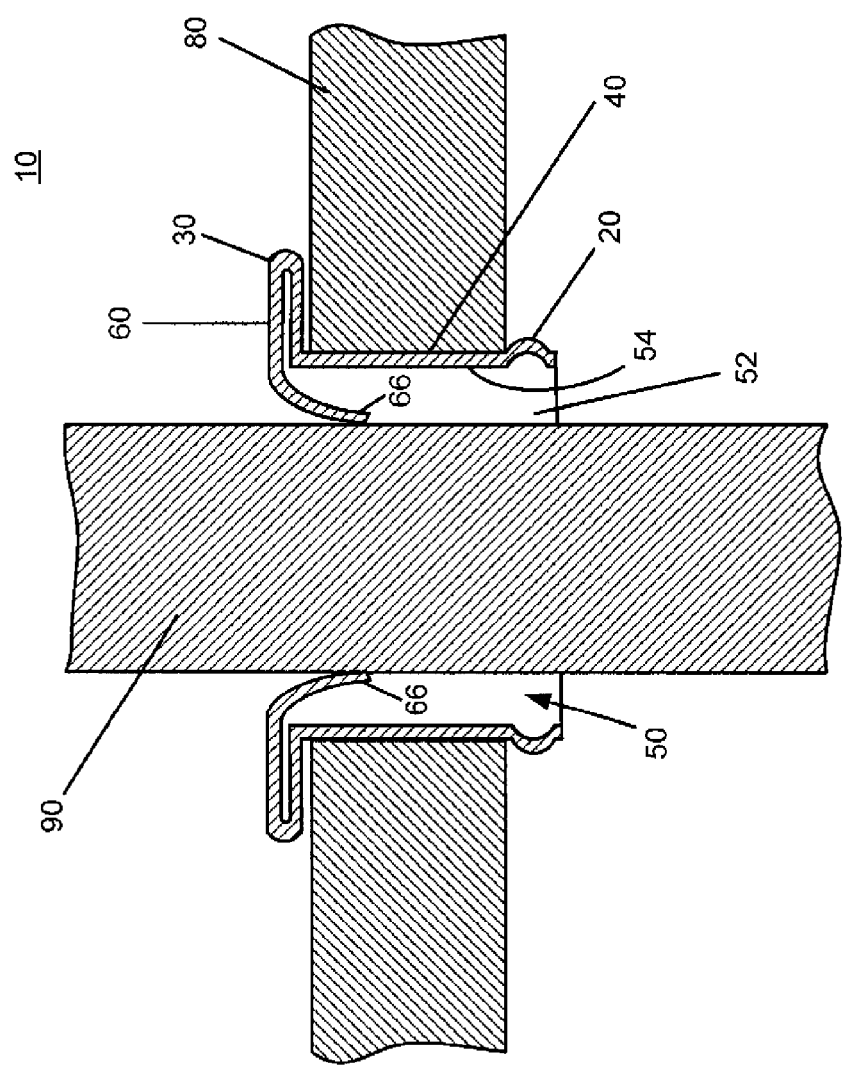
FIG. 4 is a cross-sectional view illustration of the grommet device with a medical instrument shaft, in accordance with the first exemplary embodiment of the present disclosure.

FIG. 4 is a cross-sectional view illustration of the grommet device 10 with a medical instrument shaft 90, in accordance with the first exemplary embodiment of the present disclosure. As can be seen in FIG. 4, a medical instrument shaft 90 of a medical instrument, such as a scalpel, or other tool, is shown in the inserted positioned within the device 10. In this position, the medical instrument shaft 90 moves the biasable sections 66 of the flexible top surface 60 within the aperture 50 and towards the aperture sidewall 54. Since the biasable sections 66 of the flexible top surface 60 are designed to move towards their natural, non-biased position, i.e., a position where all biasable sections 66 of the flexible top surface 60 are substantially coplanar, the biasable sections 66 of the flexible top surface 60 may naturally place a force on the medical instrument shaft 90 in an interior direction. This force may retain the medical instrument shaft 90 within the enlargeable slit 70 (FIG. 3), thereby retaining the medical instrument shaft 90 in a secure position.

Figure 5:
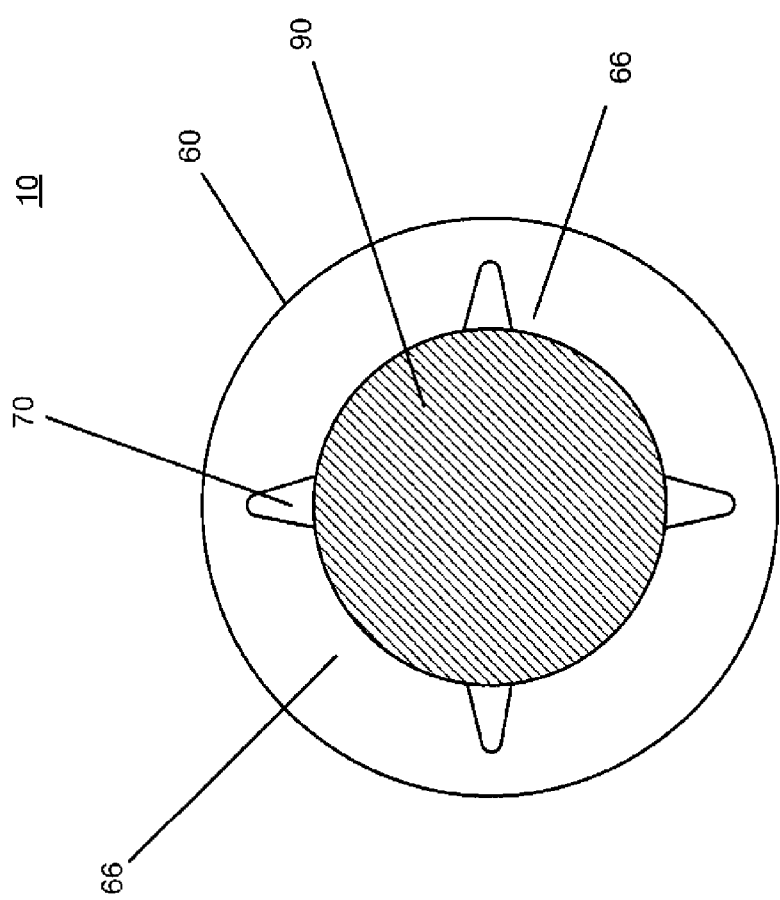
FIG. 5 is a top view illustration of the grommet device with a medical instrument shaft, in accordance with the first exemplary embodiment of the present disclosure.

FIG. 5 is a top view illustration of the grommet device 10 with a medical instrument shaft 90, in accordance with the first exemplary embodiment of the present disclosure. In particular, FIG. 5 illustrates the top view of the illustration of FIG. 4, where the medical instrument shaft 90 is inserted within the enlargeable slit 70 of the flexible top surface 60, in substantially the center point of the grommet device 10. The medical instrument shaft 90 is positioned such that it is contacted substantially equally by each of the biasable sections 66 of the flexible top surface 60. Each of the biasable sections 66 of the flexible top surface 60 may contact the medical instrument shaft 90 to secure it within the device 10. Only a small portion of the biasable sections 66 are visible in FIG. 5. Of course, the medical instrument shaft 90 may be positioned in any part of the enlargeable slit 70. For example, a medical instrument shaft 90 with a small size may bias or flex certain biasable sections 66, or portions thereof, more than other biasable sections 66 of the flexible top surface 60.

Figure 6:
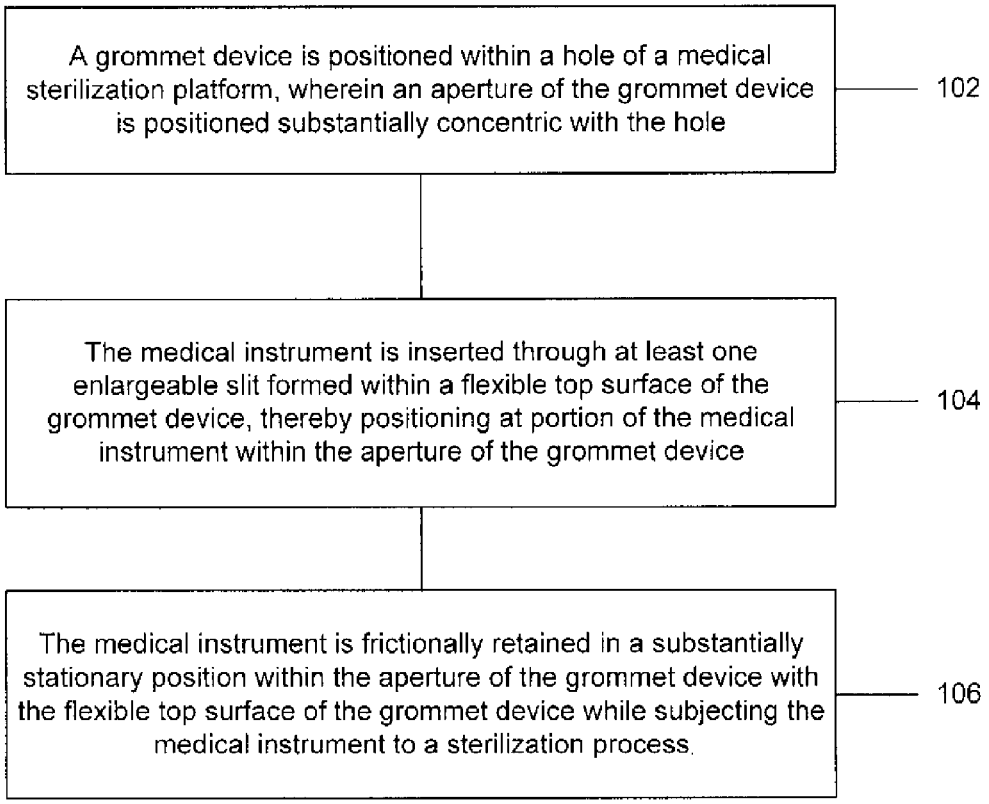
FIG. 6 is a flowchart illustrating a method of constructing a grommet device, in accordance with the first exemplary embodiment of the disclosure.

FIG. 6 is a flowchart 100 illustrating a method of securing a medical instrument with a medical sterilization platform, in accordance with a second exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 102, a grommet device is positioned within a hole of a medical sterilization platform, wherein an aperture of the grommet device is positioned substantially concentric with the hole. The medical instrument is inserted through at least one enlargeable slit formed within a flexible top surface of the grommet device, thereby positioning at portion of the medical instrument within the aperture of the grommet device (block 104). The medical instrument is frictionally retained in a substantially stationary position within the aperture of the grommet device with the flexible top surface of the grommet device while subjecting the medical instrument to a sterilization process (block 106).

The method may include any number of additional steps, processes, variations thereof, functions, or structures, including the steps, processes, functions, and structures disclosed within any embodiment of this disclosure. For example, to ensure that the grommet device can successfully support the medical instrument, the grommet device may be retained within the hole of the medical sterilization platform by sandwiching a portion of the medical sterilization platform that abuts the hole with a base structure and a top structure of the grommet device. The grommet device is removable and reusable, and as such, the grommet device may be removed from the hole within the sterilization platform by constricting the base structure and moving the base structure through the hole. When the grommet device is removed, it may first be inspected for damage and then sterilized if no damage is found. Once it is sterile, the grommet device may be reinserted into the hole within the medical sterilization platform.

To successfully frictionally retain the medical instrument within the grommet device, the grommet device may include two perpendicularly intersecting enlargeable slits formed within the flexible top surface. These two perpendicularly intersecting enlargeable slits may define four biasable sections of the flexible top surface towards the aperture, wherein the four biasable sections are each positioned between the two perpendicularly intersecting enlargeable slits. The four biasable sections may be used to contact the medical instrument and retain it in a substantially stationary position for the duration of the sterilization process, as well as before and after a sterilization process.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claim.

What is claimed is:
1. A grommet device comprising:
a substantially circular base structure;
a substantially circular top structure connected to the substantially circular base structure with a substantially cylindrical middle portion, wherein an aperture having an interior space is positioned interior of the substantially cylindrical middle portion;
a flexible top surface connected to the substantially circular top structure, wherein the flexible top surface is substantially planar; and at least one enlargeable slit formed within the flexible top surface and through an entire thickness of the flexible top surface, wherein an unobstructed path is positioned from a location proximate to an exterior side of the flexible top surface, through the at least one enlargeable slit, and into the interior space of the aperture, wherein a radial dimension of the substantially circular base structure is larger than a radial dimension of the substantially cylindrical middle portion.

2. The grommet device of claim 1, further comprising two enlargeable slits formed within the flexible top surface and through an entire thickness of the flexible top surface, wherein a first slit of the two enlargeable slits is positioned substantially perpendicular to a second slit of the two enlargeable slits.

3. The grommet device of claim 2, wherein the two enlargeable slits formed within the flexible top surface define four biasable sections of the flexible top surface.

4. The grommet device of claim 3, wherein when the four biasable sections are in a non-biased position, the two enlargeable slits are positioned between of the four biasable sections, respectively, and wherein the four biasable sections are position in a biased position, the two enlargeable slits are enlarged to create an enlarged opening to the interior space of the aperture.

5. The grommet device of claim 4, wherein in the non-biased position, the four biasable sections a substantially coplanar.

6. The grommet device of claim 1, wherein a radial dimension of the substantially circular top structure is larger than a radial dimension of the substantially cylindrical middle portion.

7. The grommet device of claim 1, wherein the at least one enlargeable slit formed within the flexible top surface substantially intersects a central axis of the aperture.

8. The grommet device of claim 1, wherein a length dimension of the at least one enlargeable slit is greater than a diameter dimension of the substantially cylindrical middle portion.

9. The grommet device of claim 1, wherein at least one enlargeable slit formed within the flexible top surface and through the entire thickness of the flexible top surface further comprises a plurality of enlargeable slits formed within the flexible top surface and through the entire thickness of the flexible top surface, wherein the plurality of enlargeable slits define a plurality of biasable sections of the flexible top surface.

10. A system for sterilizing a medical instrument comprising:
a medical instrument sterilization platform having a plurality of holes formed therein;
a grommet device positioned in one of the plurality of holes of the medical instrument sterilization platform, wherein the grommet device has a substantially circular base structure connected to a substantially circular top structure with a substantially cylindrical middle portion, wherein the substantially circular top structure is positioned on a first side of the medical instrument sterilization platform and the substantially circular base structure is positioned on a second side of the medical instrument sterilization platform, wherein the first side is positioned opposite the second side;
an aperture defined by the substantially cylindrical middle portion positioned substantially concentrically of the one of the plurality of holes; and
a flexible top surface integrally connected to the substantially circular top structure, the flexible top surface having at least one enlargeable slit formed therein, wherein the medical instrument is frictionally retained in a substantially stationary position by the flexible top surface within the at least one enlargeable slit and at least partially within the aperture, wherein a radial dimension of the substantially circular base structure is larger than a radial dimension of the substantially cylindrical middle portion.

11. The system for sterilizing a medical instrument of claim 10, wherein the at least one enlargeable slit formed within the flexible top surface further comprises two enlargeable slits formed within the flexible top surface, wherein a first slit of the two enlargeable slits is positioned substantially perpendicular to a second slit of the two enlargeable slits.

12. The system for sterilizing a medical instrument of claim 11, wherein the two enlargeable slits formed within the flexible top surface define four biasable sections of the flexible top surface, wherein the medical instrument is frictionally retained in the substantially stationary position through contact with the four biasable sections of the flexible top surface.

13. The system for sterilizing a medical instrument of claim 10, wherein when the medical instrument is frictionally retained in the substantially stationary position contacting the four biasable sections, each of the four biasable sections is positioned extending towards an interior space of the aperture.

* * * * *